United States Patent [19]

Ebner et al.

[11] Patent Number: 5,137,860
[45] Date of Patent: Aug. 11, 1992

[54] PROCESS FOR THE TRANSFORMATION OF VANADIUM/PHOSPHORUS MIXED OXIDE CATALYST PRECURSORS INTO ACTIVE CATALYSTS FOR THE PRODUCTION OF MALEIC ANHYDRIDE

[75] Inventors: Jerry R. Ebner, St. Charles; William J. Andrews, Hazelwood, both of Mo.

[73] Assignee: Monsanto Company, St. Louis, Mo.

[21] Appl. No.: 722,070

[22] Filed: Jun. 27, 1991

[51] Int. Cl.$^5$ .................. B01J 27/18; B01J 27/198
[52] U.S. Cl. .................................................. 502/209
[58] Field of Search ........................................ 502/209

[56] References Cited

U.S. PATENT DOCUMENTS

| | | | |
|---|---|---|---|
| 3,856,824 | 12/1974 | Raffelson et al. | 260/346.8 A |
| 3,862,146 | 1/1975 | Boghosian | 260/346.8 A |
| 3,864,280 | 2/1975 | Schneider | 252/435 |
| 3,888,886 | 6/1975 | Young et al. | 260/346.8 |
| 3,980,585 | 9/1976 | Kerr et al. | 252/437 |
| 4,018,709 | 4/1977 | Barone et al. | 252/435 |
| 4,187,235 | 2/1980 | Katsumoto et al. | 260/346.75 |
| 4,251,390 | 2/1981 | Barone | 252/435 |
| 4,312,787 | 1/1982 | Dolhyj et al. | 252/435 |
| 4,315,864 | 2/1982 | Bremer et al. | 260/346.75 |
| 4,333,853 | 6/1982 | Milberger et al. | 252/435 |
| 4,562,269 | 12/1985 | Moorehead | 549/259 |
| 4,567,158 | 1/1986 | Wrobleski et al. | 502/209 |
| 4,632,915 | 12/1986 | Keppel et al. | 502/209 |
| 4,632,916 | 12/1986 | Bither | 502/209 |
| 4,670,415 | 6/1987 | Keppel et al. | 502/209 |
| 4,784,981 | 11/1988 | Alpers et al. | 502/209 |

FOREIGN PATENT DOCUMENTS 0098039 1/1984 European Pat. Off. .

Primary Examiner—W. J. Shine
Attorney, Agent, or Firm—W. Brooks

[57] ABSTRACT

Vanadium/phosphorus mixed oxide catalysts comprising vanadyl pyrophosphate, optionally containing a promoter component, are transformed from vanadium/phosphorus mixed oxide catalyst precursors comprising vanadyl hydrogen phosphate, optionally containing a promoter component, by subjecting the catalyst precursors to elevated temperatures in three stages—(a) an initial heat-up stage in an atmosphere selected from the group consisting of air, steam, an inert gas, and mixtures thereof, (b) a rapid heat-up stage at a programmed heat-up rate in a molecular oxygen/steam-containing atmosphere, and (c) a maintenance/finishing stage, first in a molecular oxygen/-steam-containing atmosphere, and thereafter in a nonoxidizing, steam-containing atmosphere. Such catalysts are useful for the production of maleic anhydride via the partial oxidation of nonaromatic hydrocarbons, particularly n-butane, in the vapor phase with molecular oxygen or a molecular oxygen-containing gas.

59 Claims, No Drawings

PROCESS FOR THE TRANSFORMATION OF VANADIUM/PHOSPHORUS MIXED OXIDE CATALYST PRECURSORS INTO ACTIVE CATALYSTS FOR THE PRODUCTION OF MALEIC ANHYDRIDE

BACKGROUND OF THE INVENTION

1. Field of the Invention

This invention relates to a process for the transformation of vanadium/phosphorus mixed oxide catalyst precursors into active catalysts for the production of maleic anhydride. More particularly, this invention relates to a process for the transformation of catalyst precursors comprising vanadyl hydrogen phosphate, optionally containing a promoter component, into active catalysts comprising vanadyl pyrophosphate, also optionally containing a promoter component. The active catalysts are suitable for the production of maleic anhydride via the partial oxidation of nonaromatic hydrocarbons in the vapor phase with molecular oxygen or a molecular oxygen-containing gas.

Maleic anhydride is of significant commercial interest throughout the world. It is used alone or in combination with other acids in the manufacture of alkyd and polyester resins. It also is a versatile intermediate for chemical synthesis. Significant quantities of maleic anhydride are produced each year to satisfy these varied needs.

2. Description of the Related Art

Numerous catalysts containing vanadium, phosphorus, and oxygen (sometimes referred to as mixed oxides of vanadium and phosphorus), substantially in the form of vanadyl pyrophosphate, optionally containing a promoter component, are disclosed in the prior art as being useful for the conversion of various organic feedstocks to maleic anhydride. In general, such catalysts, wherein the valence of the vanadium is less than +5, usually between about +3.8 and about +4.8, are considered as being particularly well-suited for the production of maleic anhydride from saturated hydrocarbons having at least four carbon atoms in a straight chain (or cyclic structure). In many instances, these catalysts also contain added promoter elements or components which are considered to exist in the catalyst as oxides. Common organic feedstocks include nonaromatic hydrocarbons such as n-butane, 1- and 2-butenes, 1,3-butadiene, or mixtures thereof.

Procedures for the preparation of catalysts containing the mixed oxides of vanadium and phosphorus, optionally containing a promoter component, are also disclosed and taught by the prior art. In general, such catalysts are prepared by contacting vanadium-containing compounds, phosphorus-containing compounds, and promoter component-containing compounds (when a promoter element is desired) under conditions sufficient to reduce pentavalent vanadium to the tetravalent state and form the desired catalyst precursor comprising vanadyl hydrogen phosphate, optionally containing a promoter component. The catalyst precursor is thereafter recovered and subjected to a variety of conventional techniques well known to those skilled in the art (commonly and conveniently referred to as calcination or cognate words, such as calcine or calcined) to produce the active catalyst.

U.S. Pat. No. 4,632,916 discloses vanadium/phosphorus oxide catalysts, optionally containing a promoter component of silicon and at least one of indium, antimony, and tantalum, for the vapor-phase oxidation of n-butane to maleic anhydride. Such catalysts are prepared by (a) contacting in an aqueous or organic liquid medium a vanadium species having a valence of substantially +4 with a phosphorus species in an amount sufficient to form a catalyst precursor which will provide a phosphorus/vanadium (P/V) atom ratio in the catalyst of from about 0.9 to about 1.3, and optionally a promoter comprising silicon and at least one of indium, antimony, and tantalum in amounts sufficient to form a catalyst precursor which will provide a silicon/vanadium (Si/V) atom ratio and an (indium+antimony+tantalum)/vanadium [(In+Sb+Ta)/V] atom ratio, respectively, in the catalyst of from about 0.02 to about 3.0 and 0.005 to about 0.2, (b) blending the catalyst precursor with a pore-modifying agent in an amount of from 3% to about 5% by weight and fumed silica having a surface area of at least 150 m$^2$/g in an amount of from about 0.05% to about 0.20% by weight, and (c) heating the resultant combination to generate the catalyst.

U.S. Pat. No. 4,632,915 discloses catalysts comprising phosphorus, vanadium, and oxygen, and a promoter component containing each of iron and lithium which are useful for the partial oxidation of nonaromatic hydrocarbons, particularly n-butane, with molecular oxygen or a molecular oxygen-containing gas in the vapor phase to produce maleic anhydride in excellent yields. The catalyst precursors are calcined under conditions involving subjecting the catalyst precursor to elevated temperatures in a variety of atmospheres, including dry air, followed by water-containing air, which, in turn, is followed by hydrocarbon-containing air to yield the active catalyst.

U.S. Pat. No. 4,567,158 relates to a process for the preparation of vanadium/phosphorus mixed oxide oxidation catalysts wherein the catalysts, which exhibit a single pass weight/weight productivity of at least 70 grams of maleic anhydride (from a nonaromatic hydrocarbon) per kilogram of catalyst per hour, are produced from catalyst precursors by subjecting the catalyst precursors to elevated temperatures in an air atmosphere and/or a nitrogen/steam-containing atmosphere for a time sufficient to yield active catalyst.

U.S. Pat. No. 4,562,269 discloses large surface area oxidation catalysts suitable for the conversion of $C_4$ to $C_{10}$ hydrocarbons to maleic anhydride. Such catalysts comprise the oxides of vanadium, phosphorus, and tin in combination with a crystalline silica having a surface area between 100 m$^2$/g to 450 m$^2$/g wherein the vanadium has an average valence in the range of from about +3.5 to +4.9. The transformation of the catalyst precursor into the active catalyst is accomplished by calcination of the catalyst precursor in an air or oxygen atmosphere at a temperature of from about 204° C. (400° F.) to about 649° C. (1200° F.) for about 0.25 hour to about 6 hours, preferably from about 0.5 hour to about 4 hours.

U.S. Pat. No. 4,333,853 discloses a vanadium/phosphorus mixed oxide catalyst prepared by reducing vanadium substantially in the pentavalent valence state to a tetravalent valence state in the presence of a phosphorus-containing compound and in the absence of a corrosive reducing agent in an organic liquid medium capable of reducing the vanadium to a valence state less than +5, recovering the resultant vanadium/phosphorus mixed oxide catalyst precursor, drying such precursor, and calcining the precursor, preferably in the presence of an oxygen-containing gas, to obtain the active catalyst. Such catalysts reportedly are effective in the oxidation of $C_4$ hydrocarbons such as n-butane, 1- and 2-butenes, 1,3-butadiene, or mixtures thereof to produce maleic anhydride with selectivities ranging from 58.7% to 68.1% and yields (mol %) ranging from 51.4% to 59.5%.

U.S. Pat. No. 4,315,864 relates to a process for the production of maleic anhydride from normal $C_4$ hydrocarbons in the presence of a vanadium/phosphorus mixed oxide catalyst. The catalyst is prepared by reducing a pentavalent vanadium-containing compound in an olefinic, oxygenated organic liquid medium to a $+4$ valence in the absence of a corrosive reducing agent, recovering resultant catalyst precursor, drying the catalyst precursor, and calcining the precursor, preferably in the presence of an oxygen-containing gas, to obtain the active catalyst.

U.S. Pat. No. 4,312,787 describes a catalyst which comprises an inert support and a catalytically active mixed oxide material coating of vanadium and phosphorus or of vanadium, phosphorus, and uranium on the outer surface of the support in an amount greater than 50% to about 80% by weight of the combined support and oxide material. Catalysts within the scope of the claims of the patent were reported to produce maleic anhydride from n-butane in yields ranging from 53% to 62.5%, with selectivities ranging from 57.4% to 67.9%.

In U.S. Pat. No. 4,251,390, a zinc-promoted vanadium-phosphorus-oxygen catalyst is disclosed and claimed. The catalyst is prepared by reducing pentavalent vanadium in a substantially anhydrous organic medium to a lower valent state and digesting the reduced vanadium in the presence of a zinc promoter compound. The resultant catalyst (catalyst precursor) is activated by a rapid conditioning procedure involving heating the catalyst to a temperature of 380° C. in a stream of air at a temperature increase of 3° C. per minute, maintaining these conditions for 2 hours, and thereafter increasing the temperature to 480° C. at 4° C. per minute in the presence of a butane-in-air mixture, or alternatively by a standard conditioning procedure involving bringing the catalyst to operating temperatures for the oxidation of n-butane to maleic anhydride at a rate of 5° C. to 10° C. per hour in the presence of a butane-in-air mixture.

In U.S. Pat. No. 4,187,235, a process is described for preparing maleic anhydride from n-butane in the presence of a vanadium-phosphorus-oxygen high surface area catalyst, that is, 10 to 100 square meters per gram ($m^2/g$), as determined by the BET method. The catalyst is prepared by reducing pentavalent vanadium to a valence between $+4.0$ and $+4.6$ with a substantially anhydrous primary or secondary alcohol and contacting the reduced vanadium with phosphoric acid, followed by recovering and calcining the resultant vanadium(IV) phosphate catalyst precursor compound by heating the catalyst precursor to a temperature of 380° C. in a stream of air at a temperature increase of 3° C. per minute, maintaining these conditions for two hours, and thereafter increasing the temperature to 480° C. at 4° C. per minute in the presence of a butane-in-air mixture.

U.S. Pat. 4,018,709 discloses a process for the vapor phase oxidation of normal $C_4$ hydrocarbons using catalysts containing vanadium, phosphorus, uranium, or tungsten or a mixture of elements from zinc, chromium, uranium, tungsten, cadmium, nickel, boron, and silicon.

In a preferred embodiment, the catalyst also contains an alkali metal or an alkaline earth metal, especially lithium, sodium, magnesium, or barium as active components. Typically, the active catalysts are prepared by refluxing a reaction mixture of suitable source materials in concentrated (37%) hydrochloric acid to form a catalyst precursor. The resultant catalyst precursor is recovered, dried, and calcined in air at elevated temperatures of from about 300° C. to about 350° C.

In U.S. Pat. No. 3,980,585, a process is disclosed for the preparation of maleic anhydride from normal $C_4$ hydrocarbons in the presence of a catalyst containing vanadium, phosphorus, copper, oxygen, tellurium, or a mixture of tellurium and hafnium or uranium or a catalyst containing vanadium, phosphorus, copper, and at least one element selected from the group of tellurium, zirconium, nickel, cerium, tungsten, palladium, silver, manganese, chromium, zinc, molybdenum, rhenium, samarium, lanthanum, hafnium, tantalum, thorium, cobalt, uranium, and tin, optionally (and preferably) with an element from Groups IA (alkali metals) or IIA (alkaline earth metals). The prepared catalyst precursor is converted into the active catalyst by calcining the catalyst precursor in air at elevated temperatures of from about 300° C. to about 350° C.

U.S. Pat. No. 3,888,886 discloses a process for the oxidation of n-butane at a temperature from about 300° C. to about 600° C. with a vanadium/phosphorus/oxygen catalyst having a phosphorus/vanadium atom ratio of from about 0.5 to about 2, promoted or modified with chromium, iron, hafnium, zirconium, lanthanum, and cerium, the promoter metal/vanadium atom ratio being between about 0.0025 and about 1. The catalysts are prepared by refluxing a reaction mixture of vanadium oxide, phosphoric acid, a hydrogen halide (usually hydrochloric acid), and a specified promoter metal-containing compound to yield the corresponding catalyst precursor. The resultant catalyst precursor is recovered, dried, formed into structures—spheres, for example—and calcined in the presence of a butane-in-air mixture at about 490° C. to produce the active catalyst.

U.S. Pat. No. 3,864,280 discloses vanadium/phosphorus mixed oxide catalyst having an intrinsic surface area of from about 7 to about 50 $m^2/g$. The catalysts are prepared by precipitation of a vanadium/phosphorus/oxygen complex from an essentially organic solvent medium in the absence of gross amounts of water. The resultant crystalline precipitate is activated by heating in air, followed by a 1.5 mol % butane-in-air mixture, both at elevated temperatures.

U.S. Pat. No. 3,862,146 discloses a process for the oxidation of n-butane to maleic anhydride in the presence of a vanadium-phosphorus-oxygen catalyst complex, promoted or activated with zinc, bismuth, copper, or lithium activator, obtained by calcination of a catalyst precursor in air at elevated temperatures. The phosphorus/vanadium and activator/vanadium atom ratios are from about 0.5 to about 5 and from about 0.05 to about 0.5, respectively.

U.S Pat. No. 3,856,824 discloses a process for the production of maleic anhydride by oxidation of saturated aliphatic hydrocarbons in the presence of a catalyst comprising vanadium, phosphorus, iron, oxygen, and added modifier comprising chromium combined with at least one element selected from the group consisting of nickel, boron, silver, cadmium, and barium. The active catalysts are prepared by refluxing an aqueous slurry of suitable source materials acid to form a catalyst precursor. The resultant catalyst precursor is recovered, dried, and calcined in air, oxygen, or an inert gas, preferably air, at elevated temperatures of from about 400° C. to about 600° C.

European Patent Application No. 98,039 discloses a process for the preparation of vanadium-phosphorus mixed oxide catalysts, optionally containing an added promoter element selected from the group consisting of Group IA (alkali metals), Group IIA (alkaline earth metals), titanium, chromium, tungsten, niobium, tantalum, manganese, thorium, uranium, cobalt, molybdenum, iron, zinc, hafnium, zirconium, nickel, copper, arsenic, antimony, tellurium, bismuth, tin, germanium, cadmium, and lanthanides, and mixtures thereof. The catalysts, which exhibit a phosphorus/vanadium atom ratio of from about 0.8 to about 1.3 and a promoter/vanadium atom ratio from about 0.01 to about 0.5, are prepared in an organic liquid reaction medium capable of reducing the vanadium to a valence state of approximately +4 to form a nonsolubilized catalyst precursor, contacting the nonsolubilized catalyst precursor-containing organic liquid with water to form a two-phase system having an upper organic liquid phase and a lower nonsolubilized catalyst precursor-containing aqueous phase, drying the catalyst precursor, and calcining the precursor at a temperature of from 300° C. to 500° C. in the presence of air, hydrocarbon, an inert gas, or a mixture of steam and air to obtain the active catalyst. The catalysts so obtained reportedly are useful in the production of maleic anhydride from normal $C_4$ hydrocarbons.

The transformation of the catalyst precursor into the active catalyst, as indicated by the cited references, may be accomplished by calcination under a variety of conditions. And although the prior art processes generally are effective to provide the desired active catalyst (from the catalyst precursor), which, in turn, generally are successful in producing the desired maleic anhydride product, the commercial utility of a catalyst system and a catalytic process is highly dependent upon the cost of the catalyst employed, the conversion of the reactants, and the yield of the desired product(s), or stated differently, the actual productivity of the catalyst system. In many instances, a reduction in the cost of a catalyst system employed in a given catalytic process on the order of a few cents per kilogram or pound, or a small percent increase in the yield of the desired product, relative to the amount of catalyst required, represents a tremendous economic advantage in a commercial operation. Accordingly, research efforts are continually being made to define new or improved catalyst systems and methods and processes of making new and old catalyst systems to reduce the cost and/or upgrade the activity, selectivity, and/or productivity of such catalyst systems in such catalytic processes. The discovery of the process of the instant invention, therefore, is believed to be a decided advance in the catalyst art.

SUMMARY OF THE INVENTION

This invention is directed to a process for the transformation of vanadium/phosphorus mixed oxide catalyst precursors into active catalysts for the production of maleic anhydride. Accordingly, the primary object of this invention is to provide a process for the transformation of vanadium/phosphorus mixed oxide catalyst precursors comprising vanadyl hydrogen phosphate, optionally containing a promoter component, into active catalysts comprising vanadyl pyrophosphate, also optionally containing a promoter component, useful for the oxidation of nonaromatic hydrocarbons to produce maleic anhydride.

Another object of this invention is to provide a process for the transformation of vanadium/phosphorus mixed oxide catalyst precursors comprising vanadyl hydrogen phosphate, optionally containing a promoter component, into active catalysts comprising vanadyl pyrophosphate, also optionally containing a promoter component, useful for the production of maleic anhydride in excellent yields.

Still another object of this invention is to provide a process for the transformation of vanadium/phosphorus mixed oxide catalyst precursors comprising vanadyl hydrogen phosphate, optionally containing a promoter component, into active catalysts comprising vanadyl pyrophosphate, also optionally containing a promoter component, useful for the partial oxidation of n-butane to produce maleic anhydride in excellent yields.

These and other objects, aspects, and advantages of the instant invention will become apparent to those skilled in the art from the accompanying description and claims.

The above objects are achieved by the process of the instant invention for the transformation of a catalyst precursor represented by the formula $$VO(M)_m HPO_4 \cdot aH_2O \cdot b(P_{2/c}O) \cdot n(organics)$$

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organics component, into an active catalyst represented by the formula $$(VO)_2(M)_m P_2O_7 \cdot b(P_{2/c}O)$$

wherein M, m, b, and c are as defined above, which process comprises:
(a) heating the catalyst precursor in an atmosphere selected from the group consisting of air, steam, an inert gas, and mixtures thereof to a temperature not to exceed about 300° C.;
(b) maintaining the catalyst precursor at the temperature of Step (b) and providing an atmosphere containing molecular oxygen, steam, and optionally an inert gas, the atmosphere being represented by the formula $$(O_2)_x(H_2O)_y(IG)_z$$

wherein IG is an inert gas and x, y, and z represent mol % of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;
(c) increasing the temperature at a programmed rate of from about 2° C. per minute to about 12° C. per minute to a value effective to eliminate the water of hydration from the catalyst precursor;

(d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and (e) continuing to maintain the adjusted temperature in a nonoxidizing, steam-containing atmosphere for a time effective to complete the catalyst precursor-to-active catalyst transformation to yield the active catalyst.

DESCRIPTION OF THE PREFERRED EMBODIMENTS

In accordance with this invention, a process is provided for the transformation of vanadium/phosphorus mixed oxide catalyst precursors comprising vanadyl hydrogen phosphate, optionally containing a promoter component, into active catalysts comprising vanadyl pyrophosphate, also optionally containing a promoter component, useful for the partial oxidation of nonaromatic hydrocarbons having at least four carbon atoms in a straight chain (or cyclic structure) with molecular oxygen or a molecular oxygen-containing gas in the vapor phase to maleic anhydride. These catalysts, transformed from catalyst precursors in accordance with the process of the instant invention, exhibit enhanced catalyst activity and excellent selectivities to, and yields of, maleic anhydride, when compared to catalysts transformed from catalyst precursors via conventional procedures.

Catalysts transformed from catalyst precursors in accordance with the process of the instant invention are represented by the formula

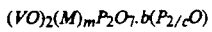

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, b is a number taken to provide a P/V atom ratio of from about 1.0 to about 1.3, and c is a number representing the oxidation number of phosphorus and has a value of 5.

The term "Periodic Table of the Elements", as employed herein, refers to the Periodic Table of the Elements (previous IUPAC form) published in CRC Handbook of Chemistry and Physics, 71st ed., Lide, Ed., CRC Press, Inc., Boca Raton, Fla., 1990, page 1-10.

Although catalysts, as represented by the formula, resulting from the transformation of the catalyst precursors are indicated as having a phosphorus-to-vanadium (phosphorus/vanadium or P/V) atom ratio of from about 1.0 to about 1.3, preferably from about 1.0 to about 1.2, most preferably from about 1.05 to about 1.15, the actual P/V atom ratio may range from a value as low as about 0.9 up to the stated value of about 1.3. The total atom ratio of promoter element-to-vanadium (promoter element/vanadium or M/V), when a promoter element is present as a component of the catalyst, in accordance with the formula representing the active catalyst, advantageously is in the range from about 0.0001 to about 0.2, preferably from about 0.0005 to about 0.1, most preferably from about 0.001 to about 0.05. These catalysts, as previously noted, exhibit enhanced catalyst activity and excellent selectivities to, and yields of, maleic anhydride, when compared to catalysts transformed from catalyst precursors via conventional procedures.

For purposes of this invention, the term "yield" means the ratio of the moles of maleic anhydride obtained to the moles of hydrocarbon feedstock introduced into the reactor multiplied by 100, the term expressed as mol %. The term "selectivity" means the ratio of moles of maleic anhydride obtained to the moles of hydrocarbon feedstock reacted or converted multiplied by 100, the term expressed as mol %. The term "conversion" means the ratio of moles of hydrocarbon feedstock reacted to the moles of hydrocarbon introduced into the reactor multiplied by 100, the term expressed as mol %. The term "space velocity" or "gas hourly space velocity" or "GHSV" means the hourly volume of gaseous feed expressed in cubic centimeters ($cm^3$) at 20° C. and atmospheric pressure, divided by the catalyst bulk volume, expressed as $cm^3/cm^3$/hour or $hr^{-1}$.

Catalyst precursors suitable for use in the process of the instant invention are those known to the art, and, in general, are materials capable of being transformed into active catalysts in accordance with the process of the instant invention which are capable of catalyzing the vapor phase partial oxidation of nonaromatic hydrocarbons to maleic anhydride under oxidation conditions. Such catalyst precursors are represented by the formula

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated or occluded organics component.

In a manner similar to that discussed previously with respect to the active catalysts, the catalyst precursors, as represented by the formula therefor, are indicated as having a phosphorus-to-vanadium (phosphorus/vanadium or P/V) atom ratio of from about 1.0 to about 1.3, preferably from about 1.0 to about 1.2. However, the actual P/V atom ratio may range from a value as low as about 0.9 up to the stated value of about 1.3. The total atom ratio of promoter element-to-vanadium (promoter element/vanadium or M/V), when a promoter element is present as a component of the catalyst precursor, in accordance with the formula representing the catalyst precursor, advantageously is in the range from about 0.0001 to about 0.2, preferably from about 0.0005 to about 0.1, most preferably from about 0.001 to about 0.05.

In those instances where the catalyst precursor is prepared in an organic reaction medium, such as, for example, primary and secondary alcohols—methanol, ethanol, 1-propanol, 2-propanol, 2-methyl-1-propanol (isobutyl alcohol), 3-methyl-2-butanol, 2,2-dimethyl-1-propanol, 1,2-ethanediol (ethylene glycol), for example—intercalated or occluded organic materials (organics), as represented by the term "n(organics)" in the formula for the catalyst precursors, may represent up to 40% by weight, or higher, typically from about 2% by weight to about 25% by weight, of the catalyst precursor composition, depending upon the conditions (temperature and time) under which the catalyst precursor is dried. For example, if the catalyst precursor is dried at about 150° C. for about 8 hours, the intercalated organic materials typically represent about 25% by weight, while drying at about 250° C. for about 4 hours typically results in a catalyst precursor having about 2% by weight intercalated organic materials. In general, the preparation of the catalyst precursors in an organic reaction medium is preferred over preparations carried out in an aqueous medium. Most preferred among suitable organic reaction media are the previously noted primary and secondary alcohols, with isobutyl alcohol being most preferred.

Specific, albeit nonlimiting, examples of suitable catalyst precursor materials are those described in several of the references previously noted in the "Description of the Related Art"—U.S. Pat. Nos. 4,632,916; 4,632,915; 4,567,158; 4,333,853; 4,315,864; 4,312,787; 4,251,390; 4,187,235; 4,018,709; 3,980,585; 3,888,866; 3,864,280; 3,862,146; and 3,856,824; and European Patent Application No. 98,039—it being understood, however, that the same are not to be construed as limiting but instead are for purposes of illustration and guidance in the practice of the process of the instant invention. These references are herein incorporated by reference. Among such catalyst precursor materials, nonlimiting examples of those preferred for use in the process of the instant invention are those described in U.S. Pat. Nos. 4,632,915 and 4,567,158.

It will be apparent to those skilled in the art that the catalyst precursor materials, once prepared, recovered, and dried, may be formed into structures, if structures are desired, suitable for use in a maleic anhydride reactor. Techniques for forming appropriate structures from the catalyst precursors for use in a fixed-bed, heat exchanger type reactor, a fluidized-bed reactor, or a transport-bed reactor are well known to those skilled in the art. For example, the catalyst precursors can be structured in unsupported form for use in a fixed-bed, heat exchanger type reactor by prilling or tableting, extruding, sizing, and the like. Suitable binding and/or lubricating agents for pelleting or tableting include starch, calcium stearate, stearic acid, and graphite. Extrusion of the catalyst precursors can be achieved by forming a wet paste which does not slump and extruding the paste. Similarly, the catalyst precursors can be comminuted for use in a fluidized-bed reactor or a transport-bed reactor.

The catalyst precursors also can be supported on support materials or carriers for use in fixed-bed, fluidized-bed, or transport-bed operations. Nonlimiting representative carriers include alumina, silica, silica-gel, silicon carbide, ceramic donuts, magnesia, titania, and titania-silica.

In operation of the process of the instant invention, the catalyst precursor is transformed into the active catalyst by a series of steps conveniently referred to as calcination. This transformation, which is critical for the preparation of superior catalysts, is accomplished in three stages. For convenience, these may be referred to as (1) initial heat-up stage, (2) rapid heat-up stage, and (3) maintenance/finishing stage.

In the initial heat-up stage, the catalyst precursor is heated in an atmosphere selected from the group consisting of air, steam, inert gas, and mixtures thereof, at any convenient heat-up rate, to a temperature not to exceed the phase transformation initiation temperature, which temperature is about 300° C. In general, suitable temperatures for the initial heat-up stage range from about 200° C. to about 300° C., with a temperature of from about 250° C. to about 275° C. being preferred.

After the desired temperature has been achieved in the initial heat-up stage, the initially selected atmosphere (in the event it does not contain molecular oxygen and steam and/or has a different composition than that which is desired for the rapid heat-up stage) is replaced by a molecular oxygen/steam-containing atmosphere, while maintaining the catalyst precursor at the temperature achieved in the initial heat-up stage. Such atmosphere optionally may contain an inert gas and, as such, may be conveniently represented by the formula $$(O_2)_x(H_2O)_y(IG)_z$$

wherein IG is an inert gas and x, y, and z represent mol % (or volume %) of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere. In a preferred embodiment, such atmosphere has a composition in which x is about 5 mol % to about 15 mol %, y is about 25 mol % to about 75 mol %, and z is zero (0) mol % to about 70 mol %, with the proviso that the sum of $(x+y+Z)$ is 100. A critical feature of the instant invention is that such atmosphere must contain at least a portion of molecular oxygen and water (as steam). The presence of the inert gas in such atmosphere, as indicated by the formula, is optional. Nonlimiting examples of suitable inert gases suitable for use in the molecular oxygen/steam-containing atmosphere include (molecular) nitrogen, helium, argon, and the like, with nitrogen generally being preferred for practicable reasons.

Once the molecular oxygen/steam-containing atmosphere is provided, the catalyst precursor is subjected to the rapid heat-up stage of the calcination. In the rapid heat-up stage, the initial heat-up stage temperature is increased at a programmed rate of from about 2° C. per minute (°C./min) to about 12° C./min, preferably from about 4° C./min to about 8° C./min, to a value effective to eliminate or remove the water of hydration from the catalyst precursor. In general, a temperature of from about 340° C. to about 450° C., usually at least about 350° C. and preferably from about 375° C. to about 425° C. is suitable.

Following the rapid heat-up stage, the catalyst precursor is subjected to the maintenance/finishing stage of calcination. In the maintenance/finishing stage, the temperature, while maintaining the molecular oxygen/steam-containing atmosphere, is adjusted to a value greater than 350° C., but less than 550° C., preferably from about 375° C. to about 450° C., most preferably from about 400° C. to about 425° C. The adjusted temperature is then maintained, first in the molecular oxygen/steam-containing atmosphere for a time effective to provide a vanadium oxidation state of from about +4.0 to about +4.5 or simply from about 4.0 to about 4.5, and thereafter in a nonoxidizing, steam-containing atmosphere, which atmosphere preferably comprises from about 25 mol % to about 75 mol % stream and from about 25 mol % to about 75 mol % inert gas, for a time effective to complete the catalyst precursor-to-active catalyst transformation to yield the active catalyst. In a manner similar to the molecular oxygen/steam-containing atmosphere, the nonoxidizing, steam-containing atmosphere also optionally may contain an inert gas, with nitrogen generally being the preferred inert gas for practicable reasons.

The nonoxidizing, steam-containing atmosphere need not necessarily be completely free of molecular oxygen. However, such atmosphere preferably is substantially free of molecular oxygen. Accordingly, molecular oxygen may be present in an amount which is not effective to cause further oxidation of the vanadium beyond the desired oxidation state of about $+4.0$ to about $+4.5$, more particularly, not beyond the maximum desired oxidation state of about $+4.5$. In general, molecular oxygen may be present in amounts which do not exceed about 0.5 mol % of the nonoxidizing, steam-containing atmosphere.

It will be apparent to those skilled in the art that the period of time during which the adjusted temperature is maintained in the molecular oxygen/steam-containing atmosphere in order to provide the desired vanadium oxidation state of from about $+4.0$ to about 4.5 will depend to some extent upon the vanadium oxidation state achieved during the rapid heat-up stage, which, in turn, will depend to some extent upon the period of time during which the catalyst precursor material is exposed to the molecular oxygen/steam-containing atmosphere at the stated rapid heat-up stage temperatures. In general, a period of time of from about 0.25 hour to about 2 hours is suitable, with a period of time of from about 0.5 hour to about 1 hour being preferred.

A suitable period of time during which the adjusted temperature is maintained in the nonoxidizing, steam-containing atmosphere is at least 1 hour, although longer periods of time up to 24 hours, or longer, may be employed, if desired, with a period of time of from about 3 hours to about 10 hours being preferred, and a period of about 6 hours being most preferred.

The active catalysts transformed from the catalyst precursors in accordance with the process of the instant invention are useful in a variety of reactors to convert nonaromatic hydrocarbons to maleic anhydride. The catalysts may be used in a fixed-bed reactor using any one or several structures known to the art, such as, for example, tablets, pellets, and the like, or in a fluid-bed or transport-bed reactor using comminuted catalyst particles, preferably having a particle size of less than about 300 microns ($\mu$m). Details of the operation of such reactors are well known to those skilled in the art.

In a preferred embodiment, the catalysts are formed into suitable structures and used in a heat transfer medium-cooled fixed-bed tube-type reactor. The details of operation of such reactors, as previously noted, are well known to those skilled in the art. The tubes of such reactors can be constructed of iron, stainless steel, carbon steel, nickel, glass, such as Vycor, and the like and can vary in diameter from about 0.635 cm (0.25 in.) to about 3.81 cm (1.50 in.) and the length can vary from about 15.24 cm (6 in.) to about 762 cm (25 ft). The oxidation reaction is highly exothermic and once reaction is underway, in order to maintain the desired reactor temperature, a heat transfer medium is necessary to conduct heat away from the reactor. Suitable heat transfer media are well known to those skilled in the art and, in general, are materials that remain in the liquid state at process temperatures and have a relatively high thermal conductivity. Examples of useful media include various heat transfer oils, molten sulfur, mercury, molten lead, and salts such as nitrates and nitrites of alkali metals, the salts being preferred due to their high boiling points. A particularly preferred heat transfer medium is a eutectic mixture of potassium nitrate, sodium nitrate and sodium nitrite which not only has a desirably high boiling point, but also, a sufficiently low freezing point that it remains in a liquid state even during periods of reactor shut-down. An additional method of temperature control is to use a metal block reactor whereby the metal surrounding the reaction zone of the reactor acts as a temperature regulating body or by conventional heat exchangers.

In general, the reaction to convert nonaromatic hydrocarbons to maleic anhydride using the catalysts transformed from the catalyst precursors in accordance with the process of the instant invention requires only contacting a nonaromatic hydrocarbon having at least four (4) carbon atoms in a straight chain (or in a cyclic structure) admixed with a molecular oxygen-containing gas (including molecular oxygen, itself), such as air or molecular oxygen-enriched air, with the catalyst at elevated temperatures. In addition to the hydrocarbon and molecular oxygen, other gases, such as nitrogen or steam, may be present or added to the reactant feedstream. Typically, the hydrocarbon is admixed with the molecular oxygen-containing gas, preferably air, at a concentration of from about 1 mol % to about 10 mol % hydrocarbon and contacted with the catalyst at a gas hourly space velocity (GHSV), or simply space velocity, of from about 100 $hr^{-1}$ up to about 5,000 $hr^{-1}$ and at a temperature of from about 300° C. to about 600° C., preferably from about 1,000 $hr^{-1}$ to about 3,000 $hr^{-1}$ and from about 325° C. to about 500° C. to produce maleic anhydride.

It is well known to those skilled in the art that the initial yield of maleic anhydride in the reaction to convert nonaromatic hydrocarbons to maleic anhydride using catalysts transformed from catalyst precursors via conventional procedures is usually low. And in such an event, such catalysts, as will occur to those skilled in the art, can be, and usually are, "conditioned" by contacting the catalysts with low concentrations of hydrocarbon and molecular oxygen-containing gas at low space velocities for a period of time before production operations begin. In contrast to the low yields of maleic anhydride customarily experienced using catalysts transformed from catalyst precursors via conventional procedures, however, catalysts transformed from catalyst precursors in accordance with the process of the instant invention do not experience such difficulties and, as a result, do not require the usual conditioning to achieve desirable yields of maleic anhydride. That is, the catalysts exhibit an immediate activity (and selectivity) sufficient to provide excellent yields of maleic anhydride without the necessity of undergoing the conditioning step usually required for catalysts transformed from catalyst precursors in accordance with conventional procedures.

Pressure is not critical in the reaction to convert nonaromatic hydrocarbons to maleic anhydride. The reaction may be conducted at atmospheric, superatmospheric, or subatmospheric pressure It generally will be preferred, however, for practical reasons, to conduct the reaction at or near atmospheric pressure. Typically, pressures of from about $1.013 \times 10^2$ kilopascals-gauge (kPa-g, 14.7 psig, 1 atm) to about $3.45 \times 10^2$ kPa-g (50.0 psig), preferably from about $1.24 \times 10^2$ kPa-g (18.0 psig) to about $2.068 \times 10^2$ kPa-g (30.0 psig), may be conveniently employed Maleic anhydride produced by using the catalysts transformed from the catalyst precursors in accordance with the process of the instant invention can be recovered by any means known to those skilled in the art. For example, maleic anhydride can be recovered by direct condensation or by absorption in suitable media with subsequent separation and purification of the maleic anhydride.

For purposes of comparing the efficiency in terms of activity, as determined by reaction (bath) temperature and maximum reaction yield of maleic anhydride, of the catalysts transformed from the catalyst precursors in accordance with the process of the instant invention with catalysts transformed from the catalyst precursors in accordance with conventional procedures not within the scope of the instant invention, the reaction temperature and maximum reaction yield values are determined by carrying out the maleic anhydride production at standardized conditions. And although any standardized set of conditions can be employed to establish the reaction temperature and maximum reaction yield values, the values reported herein, unless otherwise indicated, were determined at a hydrocarbon (n-butane)-in-synthetic air (21 mol % oxygen/79 mol % helium) concentration of $2.4 \pm 0.2$ mol % and 1,500 hr$^{-1}$ GHSV while adjusting the hydrocarbon conversion to a value, typically from about 70 mol % to about 90 mol %, usually $85 \pm 2$ mol %, sufficient to provide the highest possible yield of maleic anhydride. It will be recognized, of course, that while reaction temperature and maximum reaction yield values, as reported herein, are determined at the previously stated standardized conditions, other conditions may be employed, if desired However, reaction temperature and maximum reaction yield values determined at conditions other than $2.4 + 0.2$ mol % hydrocarbon-in-synthetic air concentration and 1,500 hr$^{-1}$ GHSV While adjusting the hydrocarbon conversion to a value sufficient to provide the highest possible yield of maleic anhydride generally will differ from those determined at the standardized conditions employed herein. As a result, direct comparison of reaction temperature and maximum reaction yield values for different catalysts may be made only if such values are determined under the same standardized conditions.

A large number of nonaromatic hydrocarbons having from four to 10 carbon atoms can be converted to maleic anhydride using the catalysts transformed from the catalyst precursors in accordance with the process of the instant invention. It is only necessary that the hydrocarbon contain not less than four carbon atoms in a straight chain or in a cyclic ring. As an example, the saturated hydrocarbon n-butane is satisfactory, but isobutane (2-methylpropane) is not satisfactory for conversion to maleic anhydride although its presence is not harmful. In addition to n-butane, other suitable saturated hydrocarbons include the pentanes, the hexanes, the heptanes, the octanes, the nonanes, the decanes, and mixtures of any of these, with or without n-butane, so long as a hydrocarbon chain having at least four carbon atoms in a straight chain is present in the saturated hydrocarbon molecule.

Unsaturated hydrocarbons are also suitable for conversion to maleic anhydride using the shaped oxidation catalyst structures of the instant invention. Suitable unsaturated hydrocarbons include the butenes (1-butene and 2-butene), 1,3-butadiene, the pentenes, the hexenes, the heptenes, the octenes, the nonenes, the decenes, and mixtures of any of these, with or without the butenes, again, so long as the requisite hydrocarbon chain having at least four carbon atoms in a straight chain is present in the molecule.

Cyclic compounds such as cyclopentane and cyclopentene also are satisfactory feed materials for conversion to maleic anhydride using the shaped oxidation catalyst structures of the instant invention.

Of the aforementioned feedstocks, n-butane is the preferred saturated hydrocarbon and the butenes are the preferred unsaturated hydrocarbons, with n-butane being most preferred of all feedstocks.

It will be noted that the aforementioned feedstocks need not necessarily be pure substances, but can be technical grade hydrocarbons.

The principal product from the oxidation of the aforementioned suitable feed materials is maleic anhydride, although small amounts of citraconic anhydride (methyl maleic anhydride) also may be produced when the feedstock is a hydrocarbon containing more than four carbon atoms.

The following specific examples illustrating the best currently-known method of practicing this invention are described in detail in order to facilitate a clear understanding of the invention. It should be understood, however, that the detailed expositions of the application of the invention, while indicating preferred embodiments, are given by way of illustration only and are not to be construed as limiting the invention since various changes and modifications within the spirit of the invention will become apparent to those skilled in the art from this detailed description.

EXAMPLE 1

Part A

This Part A illustrates a preferred procedure for the preparation of catalyst precursor materials.

A 12-liter, round bottom flask, fitted with a paddle stirrer, a thermometer, a heating mantle, and a reflux condenser, was charged with 9,000 mL of isobutyl alcohol, 378.3 g (4.20 mol) of oxalic acid ($C_2H_2O_4$), and 848.4 g (4.66 mol) of vanadium pentoxide ($V_2O_5$). To this stirred mixture was added 997.6 g (10.76 mol) of phosphoric acid ($H_3PO_4$, 105.7% by weight). The resultant mixture was refluxed for about 16 hours to give a bright blue mixture. After stripping off approximately 25% (2.2 L) of the isobutyl alcohol over a 1-hour period, the mixture was cooled and approximately 50% of the remaining isobutyl alcohol removed by decantation. The resultant concentrated slurry was then quantitatively transferred to a flat porcelain dish and dried for 24 hours at 110°–150° C. in nitrogen. The dried material was thereafter heated in air at 250°–260° C. for approximately 5 hours to yield a grey-black catalyst precursor powder.

The catalyst precursor powder was blended to contain approximately four (4.0) weight % graphite and compressed on a Stokes 512 Rotary Tableting machine equipped with appropriate dies and punches to produce the desired shaped catalyst structures, 3.97 mm cylinders having three equidistant spaced grooves etched in the longitudinal surface thereof (61% geometric volume of the corresponding solid cylinder), 3.97 mm trilobes. The compaction pressure was adjusted to produce structures with average (side) crush strengths of from 13.3N to 89N (3 lb to 20 lb). The catalyst precursor structures were transformed into active catalysts under a variety of conditions as described in Parts B-D and summarized in Table 1.

Part B

This Part B illustrates the effect of different programed heat-up rates, both within and without the scope of the instant invention, and the presence of steam in the rapid heat-up stage of the process of the instant invention.

The catalyst precursor structures of Part A were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 275° C. in air with no control of the heat-up rate. The temperature was thereafter increased in the rapid heat-up stage to 425° C. at variable programmed rates in an atmosphere of either 50 mol % air/50 mol % steam or 100% air. The temperature was maintained at 425° C. in the maintenance/finishing stage, first in the rapid heat-up stage atmosphere for a period of 1 hour, and thereafter in an atmosphere of 50 mol % nitrogen/50 mol % steam for a period of 6 hours. The parameters are summarized and tabulated in Table 1. The thusly prepared shaped catalyst structures were performance tested as described in Example 4, below.

Part C

This Part C illustrates the effects on the catalyst precursor transformation into active catalyst of a variety of atmospheres during the rapid heat-up stage and the maintenance/finishing stage of the process of the instant invention.

The catalyst precursor structures of Part A were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 275° C. in air with no control of the heat-up rate. The temperature was thereafter increased in the rapid heat-up stage to 425° C. at a programmed rate of 4° C./min in variable atmospheres. The temperature was maintained at 425° C. in the maintenance/finishing stage, first in the rapid heat-up stage atmosphere for a period of from about 0.5 hour to about 1 hour, and thereafter in a variety of molecular oxygen-free, steam-containing atmospheres for a period of 6 hours. The parameters are summarized and tabulated in Table 1. The thusly prepared shaped catalyst structures were performance tested as described in Example 4, below.

Part D

This Part D illustrates the effect on the catalyst precursor transformation into active catalyst of temperature in the maintenance/finishing stage of the process of the instant invention.

The catalyst precursor structures of Part A were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 275° C. in air with no control of the heat-up rate. The temperature was thereafter increased in the rapid heat-up stage to either 383° C. or 425° C. at a programmed rate of 4° C./min in an atmosphere of 50 mol % air/50 mol % steam. The temperature was maintained at the rapid heat-up stage temperature (either 383° C. or 425° C.) in the maintenance/finishing stage, first in the rapid heat-up stage atmosphere for a period of from about 0.5 hour to about 1 hour, and thereafter in an atmosphere of 50 mol % steam/50 mol % nitrogen for a period of 6 hours. The parameters are summarized and tabulated in Table 1. The thusly prepared shaped catalyst structures were performance tested as described in Example 4, below.

EXAMPLE 2

Part A

This Part A illustrates the preparation of a vanadium phosphorus oxide catalyst precursor having a different crystalline morphology in accordance with the procedure described for Examples 1-7 of U. S. Pat. No. 4,333,853.

A 12-liter, round bottom flask equipped as described in Example 1, Part A, above, was charged with 7,340 mL of isobutyl alcohol and 513.5 g (2.82 mol) of $V_2O_5$. Stirring was begun and a solution of 663.97 g (6.78 mol) of 100% $H_3PO_4$ in 1129 mL of isobutyl alcohol. The resultant mixture was then refluxed for about 16 hours to give a light blue mixture The mixture was cooled and the precipitate was filtered and the precipitate dried at ambient temperatures under vacuum. The dried precipitate thereafter was washed with approximately 1200 mL of isobutyl alcohol, followed by drying at 145° C. for approximately 2.5 hours to yield a dry powder.

Part B

This Part B illustrates the transformation of a catalyst precursor of the prior art into an active catalyst in accordance with the conventional procedures described in U.S. Pat. No. 4,333,853, followed by formation into desirable structures.

The dried powder from Part A was calcined for approximately 1 hour in air at 400° C. The catalyst precursor powder was blended to contain approximately four (4.0) weight % stearic acid and fed into a Stokes 512 Rotary Tableting machine equipped with appropriate dies and punches to produce the desired shaped catalyst structures, 3.97 mm trilobes. The compaction pressure was adjusted to produce structures with average (side) crush strengths of from 13.3N to 89N (3 lb to 20 lb). The thusly prepared shaped catalyst structures were performance tested as described in Example 4, below.

Part C

This Part C illustrates the transformation of a catalyst precursor of the prior art (U.S. Pat. No. 4,333,853) into an active catalyst in accordance with the process of the instant invention.

The dried powder from Part A was further dried by heating at 260° C. for 1 hour in nitrogen, followed by gradual replacement/dilution of the nitrogen atmosphere with added molecular oxygen in progressively greater amounts until an air composition of 21 mol % oxygen/79 mol % nitrogen was reached, at which point the temperature was maintained for 1 hour to yield a grey-black catalyst precursor powder. The catalyst precursor powder was blended to contain approximately four (4.0) weight % graphite and fed into a Stokes 512 Rotary Tableting machine equipped with appropriate dies and punches to produce the desired shaped catalyst structure, 3.97 mm trilobes. The compaction pressure was adjusted to produce structures with average (side) crush strengths of from 13.3N to 89N (3 lb to 20 lb). The catalyst precursor structures were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 275° C. in air with no control of the heat-up rate. The temperature was thereafter increased in the rapid heat-up stage to 425° C. at a programmed rate of 4° C./min in a 25 mol % air/50 mol % steam/25 mol % nitrogen atmosphere. The temperature was maintained at 425° C. in the maintenance/finishing stage, first in the rapid heat-up stage atmosphere for a period of 1 hour, and thereafter in an atmosphere of 50 mol % steam/50 mol % nitrogen for a period of 6 hours. The parameters are summarized and tabulated in Table 1. The thusly prepared shaped catalyst structures were performance tested as described in Example 4, below.

EXAMPLE 3

Part A

This Part A illustrates the preparation of an iron/lithium-promoted vanadium phosphorus oxide catalyst precursor in accordance with the procedure described in Example 1 of U.S. Pat. No 4,632,915, followed by formation into desirable structures.

A 12-liter, round bottom flask equipped as described in Example 1, Part A, above, except that it was further equipped with a water-cooled Dean Stark trap and a coarse-frit gas dispersion tube, was charged with 8,300 mL of isobutyl alcohol. Stirring was commenced and the isobutyl alcohol was cooled to a temperature of from about 10° C. to about 15° C. To the cooled isobutyl alcohol was added a solution of 901.8 g (7.87 mol) of 85.5% $H_3PO_4$ and 343.4 q (2.42 mol) of $P_2O_5$ maintained at room temperature. The resultant solution was cooled to a temperature of from about 5° C. to about 10° C. To this cooled solution was added, with stirring, 963.0 g (5.29 mol) of $V_2O_5$, 1.35 g (0.032 mol) of LiCl, 0.96 g (0.017 mol or g-atom) of iron powder, and an additional 1.0 L of isobutyl alcohol. Anhydrous hydrogen chloride [HCl (2037.0 g, 55.81 mol)] gas was added via the gas dispersion tube to the stirred reaction mixture over a 4.67-hour period while maintaining the temperature between 40° C. and 50° C. The solution was heated to reflux and maintained at reflux for approximately 2 hours. Thereafter, 5.4 L of distillate was removed at atmospheric pressure over a period of 5 hours, followed by an additional 1.38-hour period of reflux, followed by removal of an additional 1.5 L of distillate over a 2.36-hour period. The mixture was cooled and quantitatively transferred to a porcelain dish and dried in a box oven at 150° C. for approximately 5.5 hours. The dried material was then transferred to another box oven and heated in nitrogen at a temperature between 250° C. and 260° C. for approximately 3 hours, followed by gradual replacement of the nitrogen atmosphere by air and heating an additional 3 hours to yield a grey-black catalyst precursor powder.

The catalyst precursor powder was formed into spheres using a 50.8-cm (20-in.) rotating pan pelletizer with water spray. The spheres were dried at 165° C. in air in a continuous mesh belt furnace. The residence time in the mesh belt furnace was approximately 0.083 hour (5 min). The resultant dried spheres were screened to yield spheres having a diameter of from about 4.0 mm to about 8.0 mm.

Part B

This Part B illustrates the transformation of a catalyst precursor of the prior art, in the form of desirable structures, into an active catalyst in accordance with the conventional procedures described in U.S. Pat. No. 4,632,915.

The thusly prepared shaped catalyst (precursor) structures were activated according to the activation procedure described in U.S. Pat. No. 4,632,915, except that the structures (12.0 g) were charged to a 1.092 cm inside diameter×30.48 cm long (0.43 in. inside diameter×1 ft long) fixed bed stainless steel tubular reactor. Following the activation, the shaped catalyst structures were conditioned by warming the reactor at 1° C. per hour to 400° C. (280° C. in dry air) while passing a gas stream containing 0.6 mol % n-butane in air over the shaped catalyst structures, beginning at approximately 280° C. After the temperature had reached 400° C., the shaped catalyst structures were aged by passing the n-butane-in-air stream over the catalyst for approximately 24 hours. The thusly activated and conditioned shaped catalyst structures were performance tested as described in Example 4, below, except that the reaction was carried out at 1.5 mol % butane, 1150 GHSV, and 88 mol % butane conversion.

Part C

This Part C illustrates the transformation of a catalyst precursor of the prior art (U.S. Pat. No. 4,632,915), in the form of desirable structures, into an active catalyst in accordance with transformation procedures patterned after, but outside the scope of, the process of the instant invention.

Catalyst precursor structures prepared as described in Part A, above, but with a P/V atom ratio of 1.15, were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 250° C. in air with no control of the heat-up rate. The temperature was thereafter increased in the rapid heat-up stage to 425° C. at a programmed rate of 25° C./min in an atmosphere of 100% air. The temperature was maintained at 425° C. in the maintenance/finishing stage, first in the rapid heat-up stage atmosphere for a period of about 1.4 hours, and thereafter in an atmosphere of 50 mol % steam/50 mol % nitrogen for a period of 6 hours The parameters are summarized and tabulated in Table 1. The thusly prepared shaped catalyst structures were performance tested as described in Example 4, below, except that the reaction was carried out at 1.5 mol % butane, 1150 GHSV, and 88 mol % butane conversion.

Part D

This Part D illustrates the transformation of a catalyst precursor of the prior art (U.S. Pat. No. 4,632,915) into an active catalyst in accordance with the process of the instant invention.

Catalyst precursor structures prepared as described in Part A, above, but with a P/V atom ratio of 1.15, were placed onto a 30.48 cm×30.48 cm×2.54 cm tray formed from stainless steel mesh screen having approximately 40% open area stainless steel and placed in a box oven. The structures were heated in the initial heat-up stage from room temperature (approximately 25° C.) to 275° C. in air with no control of the heat-up rate. The temperature was thereafter increased in the rapid heat-up stage to 425° C. at a programmed rate of 4° C./min in a 75 mol % air/25 mol % steam atmosphere. The temperature was maintained at 425° C. in the maintenance/finishing stage, first in the rapid heat-up stage atmosphere for a period of 1 hour, and thereafter in an atmosphere of 50 mol % steam/50 mol % nitrogen for a period of 6 hours. The parameters are summarized and tabulated in Table 1. The thusly prepared shaped catalyst structures were performance tested as described in Example 4, below, except that the reaction was carried out at 1.5 mol % butane, 1150 GHSV, and 88 mol % butane conversion.

each catalyst when the catalyst was running at 85±2 mol % n-butane conversion. The parameters and results are tabulated in Table 2.

TABLE 2

| Catalyst | n-Butane mol % | GHSV, hr$^{-1}$ | Bath Temp, °C. | Conversion mol % | Selectivity mol % | Yield mol % |
|---|---|---|---|---|---|---|
| 1-b-1[1] | 2.4 | 1500 | 436 | 85 | 64 | 54 |
| 1-B-1-a[1] | 2.4 | 1500 | 445 | 85 | 58 | 49 |
| 1-B-2 | 2.4 | 1500 | 421 | 85 | 65 | 55 |
| 1-B-2-a[1] | 2.4 | 1500 | 440 | 85 | 64 | 54 |
| 1-B-3 | 2.4 | 1500 | 400 | 85 | 68 | 58 |
| 1-B-3-a[1] | 2.4 | 1500 | 424 | 85 | 66 | 56 |
| 1-B-4 | 2.4 | 1500 | 415 | 85 | 67 | 57 |
| 1-B-5 | 2.4 | 1500 | 416 | 85 | 64 | 54 |
| 1-B-6 | 2.4 | 1500 | 415 | 85 | 65 | 55 |
| 1-B-6-a[1] | 2.4 | 1500 | 428 | 85 | 65 | 55 |
| 1-C-1[1] | 2.4 | 1500 | 426 | 85 | 62 | 53 |
| 1-C-2 | 2.4 | 1500 | 406 | 85 | 69 | 59 |
| 1-C-3 | 2.4 | 1500 | 406 | 85 | 68 | 58 |
| 1-C-4 | 2.4 | 1500 | 413 | 85 | 68 | 58 |
| 1-C-5 | 2.4 | 1500 | 404 | 85 | 67 | 57 |
| 1-D-1 | 2.4 | 1500 | 419 | 85 | 69 | 59 |
| 1-D-2 | 2.4 | 1500 | 408 | 85 | 68 | 58 |
| 2-B[1] | 2.4 | 1500 | 419 | 85 | 65 | 55 |
| 2-C | 2.4 | 1500 | 420 | 85 | 68 | 58 |
| 3-B[1] | 1.5 | 1150 | 421 | 88 | 60 | 53 |
| 3-C[1] | 1.5 | 1150 | 428 | 88 | 66 | 58 |
| 3-D | 1.5 | 1150 | 398 | 88 | 68 | 60 |

[1]Comparative.

TABLE 1

| | Initial Heat-up Stage | | Rapid Heat-up Stage | | | Maintenance/Finishing Stage | | | | |
|---|---|---|---|---|---|---|---|---|---|---|
| | Temp, °C. | Atmosphere mol % | Temp, °C. | Atmosphere mol % | Prog Rate, °C./min | Temp, °C. | Atmosphere, mol % | | Time, hr | |
| Catalyst | | | | | | | Initial | Final | Initial | Final |
| 1-B-1[1] | 275 | 100 Air | 425 | 50 Air/50 Steam | 1 | 425 | 50 Air/50 Steam | 50 Steam/50 N$_2$ | 1 | 6 |
| 1-B-1-a[1] | 275 | 100 Air | 425 | 100 Air | 1 | 425 | 100 Air | 50 steam/50 N$_2$ | 1 | 6 |
| 1-B-2 | 275 | 100 Air | 425 | 50 Air/50 Steam | 2 | 425 | 50 Air/50 Steam | 50 Steam/50 N$_2$ | 1 | 6 |
| 1-B-2-a[1] | 275 | 100 Air | 425 | 100 Air | 2 | 425 | 100 Air | 50 Steam/50 N$_2$ | 1 | 6 |
| 1-B-3 | 275 | 100 Air | 425 | 50 Air/50 Steam | 4 | 425 | 50 Air/50 Steam | 50 Steam/50 N$_2$ | 1 | 6 |
| 1-B-3-a[1] | 275 | 100 Air | 425 | 100 Air | 4 | 425 | 100 Air | 50 Steam/50 N$_2$ | 1 | 6 |
| 1-B-4 | 275 | 100 Air | 425 | 50 Air/50 Steam | 8 | 425 | 50 Air/50 Steam | 50 Steam/50 N$_2$ | 1 | 6 |
| 1-B-5 | 275 | 100 Air | 425 | 50 Air/50 Steam | 12 | 425 | 50 Air/50 Steam | 50 Steam/50 N$_2$ | 1 | 6 |
| 1-B-6[1] | 275 | 100 Air | 425 | 50 Air/50 Steam | 25 | 425 | 50 Air/50 Steam | 50 Steam/50 N$_2$ | 1 | 6 |
| 1-B-6-a[1] | 275 | 100 Air | 425 | 100 Air | 25 | 425 | 100 Air | 50 Steam/50 N$_2$ | 1 | 6 |
| 1-C-1[1] | 275 | 100 Air | 425 | 75 Steam/25 N$_2$ | 4 | 425 | 75 Steam/25 N$_2$ | 75 Steam/25 N$_2$ | 0.5–1 | 6 |
| 1-C-2 | 275 | 100 Air | 425 | 25 Air/75 Steam | 4 | 425 | 25 Air/75 Steam | 75 Steam/25 N$_2$ | 0.5–1 | 6 |
| 1-C-3 | 275 | 100 Air | 425 | 25 Air/25 Steam/50 N$_2$ | 4 | 425 | 25 Air/25 Steam/50 N$_2$ | 50 Steam/50 N$_2$ | 0.5–1 | 6 |
| 1-C-4 | 275 | 100 Air | 425 | 50 Air/25 Steam/25 N$_2$ | 4 | 425 | 50 Air/25 Steam/25 N$_2$ | 50 Steam/50 N$_2$ | 0.5–1 | 6 |
| 1-C-5 | 275 | 100 Air | 425 | 75 Air/25 Steam | 4 | 425 | 75 Air/25 Steam | 25 Steam/75 N$_2$ | 0.5–1 | 6 |
| 1-D-1 | 275 | 100 Air | 383 | 50 Air/50 Steam | 4 | 383 | 50 Air/50 Steam | 50 Steam/50 N$_2$ | 0.5–1 | 6 |
| 1-D-2 | 275 | 100 Air | 400 | 50 Air/50 Steam | 4 | 400 | 50 Air/50 Steam | 50 Steam/50 N$_2$ | 0.5–1 | 6 |
| 2-B[1,2] | — | — | — | — | — | — | — | — | — | — |
| 2-C | 275 | 100 Air | 425 | 25 Air/50 Steam/25 N$_2$ | 4 | 425 | 25 Air/50 Steam/25 N$_2$ | 50 Steam/50 N$_2$ | 1 | 6 |
| 3-B[1,3] | — | — | — | — | — | — | — | — | — | — |
| 3-C[1,4] | | | | | | 425 | 100 Air | 50 Steam/50 N$_2$ | 1.4 | 6 |
| 3-D | | | | | | 425 | 75 Air/25 Steam | 50 Steam/50 N$_2$ | 1 | 6 |

[1]Comparative.
[2]Calcined at 400° C. in air for approximately 1 hour as described in U.S. Pat. No. 4,333,853.
[3]Transformed in accordance with the activation and conditioning procedures described in U.S. Pat. No. 4,632,915.
[4]Transformed in accordance with procedures patterned after, but outside the scope of, the process of the instant invention by the absence of steam as a component of the Rapid Heat-Up Stage atmosphere and a programmed heat-up rate of 25° C.

EXAMPLE 4

Each catalyst, unless otherwise indicated, was performance tested at a standardized set of reaction conditions—2.4±0.2 mol % n-butane in synthetic air (21 mol % oxygen/71 mol % helium), 1.034×10$^2$ kPa-g (15.0 psig) inlet pressure, and 1,500 GHSV. The catalyst of interest (12.0 g) was charged to a 1.092 cm inside diameter×30.48 cm long (0.43 in. inside diameter×1 ft long) reactor to provide a catalyst bed of approximately 15.24 cm (6 in.) in length. The catalyst was run for a period of time from about 20 hours to about 100 hours, unless otherwise indicated, at the standardized performance test conditions prior to determining the reaction (bath) temperature and reaction yield. The reaction (bath) temperature and maximum yield were determined for Comparison of the reaction temperature observed with the various catalyst materials [compare Catalysts 1-B-2, 1-B-3, 1-B-4, 1-B-5, and 1-B-6 (lower bath temperatures) with 1-B-1, 1-B-1-a, 1-B-2-a, 1-B-3-a, and 1-B-6-a (higher bath temperatures); 1-C-2, 1-C-3, 1-C-4, and 1-C-5 (lower bath temperatures) with 1-C-1 (higher bath temperature); 3-D (lower bath temperature) with 3-B and 3-C (higher bath temperatures); and 2-C with 2-B (equivalent bath temperatures)] clearly demonstrates the advantages of the catalysts transformed from catalyst precursors in accordance with the process of the instant invention over catalysts transformed from catalyst precursors in accordance with conventional procedures. In general, a similar comparison of mol % yield of maleic anhydride [compare Catalysts 1-B-2, 1-B-3, 1-B-4, 1-B-5, and 1-B-6 (higher yields) with 1-B-1, 1-B-1-a, 1-B-2-a, 1-B-3-a, and 1-B-6-a (lower yields); 1-C-2, 1-C-3, 1-C-4, and 1-C-5 (higher yields) with 1-C-1 (lower yield); 2-C (higher yield) with 2-B (lower yield); and 3-D (higher yield) with 3-B and 3-C (lower yields)] demonstrates superior performance of the catalysts formed in accordance with the catalyst precursor transformation process of the instant invention over catalysts formed in accordance with conventional catalyst precursor transformation procedures. As a result, the combined advantages of greater reaction yield at equivalent or lower reaction temperature provides a significant economic advantage.

Thus, it is apparent that there has been provided, in accordance with the instant invention, a process for the transformation of catalyst precursors into active catalysts that fully satisfies the objects and advantages set forth hereinabove. While the invention has been described with respect to various specific examples and embodiments thereof, it is understood that the invention is not limited thereto and many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for the transformation of a catalyst precursor represented by the formula $$VO(M)_m HPO_4 \cdot aH_2O \cdot b(P_2/cO) \cdot n(organics)$$

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from zero (0) to about 0.2, a is a number of at least about 0.5, b is a number taken to provide a P/V atom ratio of from about 1.0 to about 1.3, c is a number representing the oxidation number of phosphorus and has a value of 5, and n is a number taken to represent the weight % of intercalated organics component, into an active catalyst represented by the formula $$(VO)_2(M)_m P_2O_7 \cdot b(P_2/cO)$$

wherein M, m, b, and c are as defined above, which process comprises:
 (a) heating the catalyst precursor in an atmosphere selected from the group consisting of air, steam, inert gas, and mixtures thereof to a temperature not to exceed about 300° C.;
 (b) maintaining the catalyst precursor at the temperature of Step (a) and providing an atmosphere containing molecular oxygen, steam, and optionally an inert gas, the atmosphere being represented by the formula $$(O_2)_x(H_2O)_y(IG)_z$$

wherein IG is an inert gas and x, y, and z represent mol percent of the $O_2$, $H_2O$, and IG components, respectively, in the molecular oxygen/steam-containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;
 (c) increasing the temperature at a programmed rate of from about 2° C./min to about 12° C./min to a value effective to eliminate the water of hydration from the catalyst precursor;
 (d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and
 (e) continuing to maintain the adjusted temperature in a nonoxidizing, steam-containing atmosphere for a time effective to complete the catalyst precursor-to-active catalyst transformation to yield the active catalyst.

2. The process of claim 1 wherein a is about 0.5, b is a number taken to provide a P/V atom ratio of from about 1.05 to about 1.15, and n is a number up to about 40.

3. The process of claim 2 wherein n is from about 2 to about 25.

4. The process of claim 1 wherein the atmosphere in Step (a) is air.

5. The process of claim 1 wherein the catalyst precursor is heated in Step (a) to a temperature of from about 200° C. to about 300° C.

6. The process of claim 5 wherein the temperature is from about 250° C. to about 275° C.

7. The process of claim 1 wherein the molecular oxygen/steam-containing atmosphere provided in Step (b) has a composition in which x is about 5 mol % to about 15 mol %, y is about 25 mol % to about 75 mol %, and z is zero (0) to about 70 mol %, with the proviso that the sum of (x+y+z) is 100.

8. The process of claim 7 wherein the molecular oxygen is provided as air.

9. The process of claim 7 wherein the inert gas is selected from the group consisting of nitrogen, helium, argon, and mixtures thereof.

10. The process of claim 9 wherein the inert gas is nitrogen.

11. The process of claim 1 wherein the temperature is increased in Step (c) to a value of from about 350° C. to about 450° C.

12. The process of claim 11 wherein the temperature is increased to a value of from about 375° C. to about 426° C.

13. The process of claim 1 wherein the temperature is increased in Step (c) at the programmed rate of from about 4° C./min to about 8° C./min.

14. The process of claim 1 wherein the temperature is adjusted in Step (d) to a value of from about 375° C. to about 450° C.

15. The process of claim 14 wherein the temperature is adjusted to a value of from about 400° C. to about 450° C.

16. The process of claim 1 wherein the molecular oxygen/steam-containing atmosphere provided in Step (d) has a composition in which x is about 5 mol % to about 15 mol %, y is about 25 mol % to about 75 mol %, and z is zero (0) to about 70 mol %, with the proviso that the sum of (x+y+z) is 100.

17. The process of claim 16 wherein the molecular oxygen is provided as air.

18. The process of claim 16 wherein the inert gas is selected from the group consisting of nitrogen, helium, argon, and mixtures thereof.

19. The process of claim 18 wherein the inert gas is nitrogen.

20. The process of claim 1 wherein the temperature in Step (d) is maintained for a period of from about 0.25 hour to about 2 hours.

21. The process of claim 20 wherein the period is from about 0.5 hour to about 1 hour.

22. The process of claim 1 wherein the nonoxidizing, steam-containing atmosphere provided in Step (e) comprises from about 25 mol % to about 75 mol % steam and from about 25 mol % to about 75 mol % inert gas.

23. The process of claim 22 wherein the inert gas is selected from the group consisting of nitrogen, helium, argon, and mixtures thereof.

24. The process of claim 23 wherein the inert gas is nitrogen.

25. The process of claim 22 wherein the nonoxidizing, steam-containing atmosphere further comprises molecular oxygen in an amount not to exceed about 0.5 mol %.

26. The process of claim 1 wherein the temperature in Step (e) is maintained for a period of from about 1 hour to about 24 hours, or longer.

27. The process of claim 26 wherein the period is from about 3 hours to about 10 hours.

28. The process of claim 27 wherein the period is about 6 hours.

29. A process for the transformation of a catalyst precursor represented by the formula $$VO(M)_m HPO_4 \cdot aH_2O \cdot b(P_2/cO) \cdot n(organics)$$
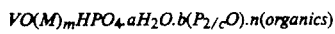

wherein M is at least one promoter element selected from the group consisting elements from Groups IA, IB, IIA, IIB, IIIA, IIIB, IVA, IVB, VA, VB, VIA, VIB, and VIIIA of the Periodic Table of the Elements, and mixtures thereof, m is a number from 0.0001 to about 0.2, a is a number of at least about 0.5, b is a number from taken to provide a P/V atom ratio of from about 1.0 to about 1.3, c is a number representing the oxidation number of phosphorus and has a value of 5, and n is a number taken to represent the weight % of intercalated organics component, into an active catalyst represented by the formula $$(VO)_2(M)_m P_2O_7 \cdot b(P_2/cO)$$
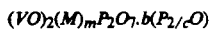

wherein M, m, b, and c are as defined above, which process comprises:
(a) heating the catalyst precursor in an atmosphere selected from the group consisting of air, steam, inert gas, and mixtures thereof to a temperature not to exceed about 300° C.;
(b) maintaining the catalyst precursor at the temperature of Step (a) and providing an atmosphere containing molecular oxygen, steam, and optionally an inert gas, the atmosphere being represented by the formula $$(O_2)_x(H_2O)_y(IG)_z$$
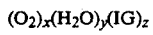

wherein IG is an inert gas and x, y, and z represent mol percent of the $O_2$, $H_2O$, and IG components, respectively, in the molecular oxygen/steam containing atmosphere, with x having a value greater than zero (0) mol %, but less than 100 mol %, y having a value greater than zero (0) mol %, but less than 100 mol %, and z having a value representing the balance of the molecular oxygen/steam-containing atmosphere;
(c) increasing the temperature at a programmed rate of from about 2° C./min to about 12° C./min to a value effective to eliminate the water of hydration from the catalyst precursor; (d) adjusting the temperature from Step (c) to a value greater than 350° C., but less than 550° C., and maintaining the adjusted temperature in the molecular oxygen/steam-containing atmosphere for a time effective to provide a vanadium oxidation state of from about +4.0 to about +4.5; and
(e) continuing to maintain the adjusted temperature in a nonoxidizing, steam-containing atmosphere for a time effective to complete the catalyst precursor-to-active catalyst transformation to yield the active catalyst.

30. The process of claim 29 wherein M is selected from Groups IA and VIIIA of the Periodic Table of the Elements, and mixtures thereof.

31. The process of claim 30 wherein M is a mixture of lithium from Group IA and iron from Group VIIIA of the Periodic Table of the Elements.

32. The process of claim 31 wherein m is from about 0.001 to about 0.05.

33. The process of claim 29 wherein a is about 0.5, b is a number taken to provide a P/V atom ratio of from about 1.05 to about 1.15, and n is a number up to about 40.

34. The process of claim 33 wherein n is from about 2 to about 25.

35. The process of claim 29 wherein the atmosphere in Step (a) is air.

36. The process of claim 29 wherein the catalyst precursor is heated in Step (a) to a temperature of from about 200° C. to about 300° C.

37. The process of claim 36 wherein the temperature is from about 250° C. to about 275° C.

38. The process of claim 29 wherein the molecular oxygen/steam-containing atmosphere provided in Step (b) has a composition in which x is about 5 mol % to about 15 mol %, y is about 25 mol % to about 75 mol %, and z is zero (0) to about 70 mol %, with the proviso that the sum of (x+y+z) is 100.

39. The process of claim 38 wherein the molecular oxygen is provided as air.

40. The process of claim 38 wherein the inert gas is selected from the group consisting of nitrogen, helium, argon, and mixtures thereof.

41. The process of claim 40 wherein the inert gas is nitrogen.

42. The process of claim 29 wherein the temperature is increased in Step (c) to a value of from about 340° C. to about 450° C.

43. The process of claim 42 wherein the temperature is increased to a value of from about 375° C. to about 425° C.

44. The process of claim 29 wherein the temperature is increased in Step (c) at the programmed rate of from about 4° C./min to about 8° C./min.

45. The process of claim 29 wherein the temperature is adjusted in Step (d) to a value of from about 375° C. to about 450° C.

46. The process of claim 45 wherein the temperature is adjusted to a value of from about 400° C. to about 450° C.

47. The process of claim 29 wherein the molecular oxygen/steam-containing atmosphere provided in Step (d) has a composition in which x is about 5 mol % to about 15 mol %, y is about 25 mol % to about 75 mol %, and z is zero (0) to about 70 mol %, with the proviso that the sum of (x+y+z) is 100.

48. The process of claim 47 wherein the molecular oxygen is provided as air.

49. The process of claim 47 wherein the inert gas is selected from the group consisting of nitrogen, helium, argon, and mixtures thereof.

50. The process of claim 49 wherein the inert gas is nitrogen.

51. The process of claim 29 wherein the temperature in Step (d) is maintained for a period of from about 0.25 hour to about 2 hours.

52. The process of claim 51 wherein the period is from about 0.5 hour to about 1 hour.

53. The process of claim 29 wherein the nonoxidizing, steam-containing atmosphere provided in Step (e) comprises from about 25 mol % to about 75 mol % steam and from about 25 mol % to about 75 mol % inert gas.

54. The process of claim 53 wherein the inert gas is selected from the group consisting of nitrogen, helium, argon, and mixtures thereof.

55. The process of claim 54 wherein the inert gas is nitrogen.

56. The process of claim 53 wherein the nonoxidizing, steam-containing atmosphere further comprises molecular oxygen in an amount not to exceed about 0.5 mol %.

57. The process of claim 29 Wherein the temperature in Step (e) is maintained for a period of from about 1 hour to about 24 hours, or longer.

58. The process of claim 57 wherein the period is from about 3 hours to about 10 hours.

59. The process of claim 58 wherein the period is about 6 hours.

* * * * *

UNITED STATES PATENT AND TRADEMARK OFFICE
CERTIFICATE OF CORRECTION

PATENT NO. : 5,137,860

DATED : Aug. 11, 1992

INVENTOR(S) : JERRY R. EBNER ET AL

It is certified that error appears in the above-identified patent and that said Letters Patent is hereby corrected as shown below:

In column 9, line 32, delete "Will" and insert --will--.

In column 10, line 32, delete (x + y + Z) and insert --(x + y + z)--.

In column 10, line 68, delete "stream" and insert --steam--.

In column 19, Table 1, after line 45, add the following to columns 2, 3, 4, 5, and 6, respectively:

```
  --250    100 Air    425    100 Air25           25
    275    100 Air    425    75 Air/25 Steam     4--
```

In column 22, line 52, delete "350°" and insert --340° --.

In column 22, line 56, delete "426°" and insert --425°--.

In column 22, line 65, delete "450°" and insert --425° --.

UNITED STATES PATENT AND TRADEMARK OFFICE
CERTIFICATE OF CORRECTION

PATENT NO. : 5,137,860

DATED : August 11, 1992

INVENTOR(S) : Jerry R. Ebner et al

It is certified that error appears in the above-indentified patent and that said Letters Patent is hereby corrected as shown below:

In Column 26, line 16, delete "Wherein" and insert --wherein--.

Signed and Sealed this

Twenty-ninth Day of March, 1994

Attest:

BRUCE LEHMAN

*Attesting Officer*     *Commissioner of Patents and Trademarks*